United States Patent [19]

Kumbrant

[11] 4,137,774
[45] Feb. 6, 1979

[54] SAMPLING MOULD

[76] Inventor: Lars A. T. Kumbrant, Box 23, S-190 63 Orsundsbro, Enköping, Sweden

[21] Appl. No.: 783,039

[22] Filed: Mar. 30, 1977

[30] Foreign Application Priority Data

Apr. 1, 1976 [SE] Sweden ............................. 7603909

[51] Int. Cl.$^2$ ............................. G01N 1/12; B28B 7/34
[52] U.S. Cl. ............................. 73/425.4 R; 73/DIG. 9
[58] Field of Search ............................. 249/DIG. 4, 62, 103; 73/DIG. 9, 425.4 R, 425.2, 425.4 P

[56] References Cited

U.S. PATENT DOCUMENTS

| 2,836,979 | 6/1958 | Ryley | 73/425.4 P |
|---|---|---|---|
| 3,489,012 | 1/1970 | Niskin | 73/425.4 R |
| 3,583,236 | 6/1971 | Taylor | 73/DIG. 9 |
| 3,704,621 | 12/1972 | Zickefoose | 73/425.4 R |
| 3,751,986 | 8/1973 | Boron | 73/425.4 R |
| 3,913,404 | 10/1975 | Boron | 73/425.4 R |
| 3,915,014 | 10/1975 | Judge et al. | 73/DIG. 9 |
| 3,934,639 | 1/1976 | McCrainor | 249/103 |
| 4,002,073 | 1/1977 | Collins | 73/DIG. 9 |
| 4,007,640 | 2/1977 | Boron | 73/DIG. 9 |
| 4,084,441 | 4/1978 | McDevitt | 73/425.4 R |

FOREIGN PATENT DOCUMENTS

1038278  8/1966  United Kingdom ............... 73/DIG. 9

Primary Examiner—Richard B. Lazarus
Assistant Examiner—John S. Brown
Attorney, Agent, or Firm—Witherspoon, Lane & Hargest

[57] ABSTRACT

Sampling mould for drawing samples of molten material from pools of molten materials, e.g. steel samples, and consisting of two parts of which at least one is provided with a recess which forms a specimen, said two parts being located and fastened to each other, and an entrance passage which through a channel permits the molten metal to flow into the recess, wherein at least one cavity, which forms a hollow of a fixed size, is provided in at least one of said two parts, said cavity or cavities being connected to the hollow forming the specimen through a channel.

6 Claims, 1 Drawing Figure

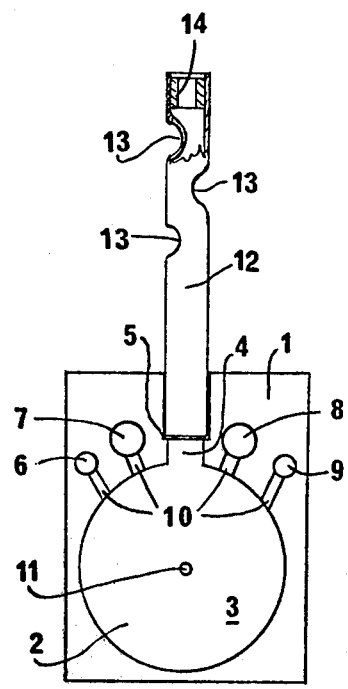

SAMPLING MOULD

The present invention relates to the field of drawing samples from pools of molten materials and is more closely defined to a sampling mould for withdrawing samples from oven and ladle, said samples being shaped like plates with handles.

It is previously known to draw samples from pools of molten materials, said samples being shaped like lollipops with a usually round flat section, and a peg protruding out from said round section. One side of the round flat section or disc is tooled to permit analysis by means of spectrometre processes and the peg is cut into suitable lengths for determining e.g. content of oxygen, carbon, sulphur etc.

Considering that the analysis results should be obtained as quickly as possible it is important that the actual sample is shaped such that a minimum of tooling is required previous to the analysis. Furthermore, the size of the samples has been standardized for combustion-methodical determination of inter alia carbon and sulphur, to 0.5 and 1 gram respectively with a tolerable deviation of approximately ±10%. To cut the peg into lengths corresponding to approximately 0.5 and 1 gram will at that occasion turn out to be rather difficult, even if a certain compensation can be made for deviations in weight.

At the drawing of certain samples of unkilled material it is preferred that the killing or deoxidizing of the samples is performed in connection with the actual sampling. To perform this killing, aluminum or another suitable metal is added in the shape of a wire or lining to the sampling device. To perform an effective killing it has, however, become necessary to provide the sampling device with specific turbulence chambers, which have improved the mixing of the samples.

The object of the present invention is to set aside the disadvantages of previously known sampling apparatuses. This object is reached by means of a sampling device of a kind as stated in the claims, from which the specific characteristics of the invention also appear.

The invention is described in greater detail below, with reference to the attached drawing, which schematically illustrates one half of a divided mould according to the present invention.

In a preferred embodiment of the sampling mould according to the present invention, said sampling mould consists of two essentially identical mould halves 1, one of which is illustrated in the drawing.

The illustrated mould half 1 consists of a parallelepipedically shaped block in which a circular recess 2 with a flat bottom 3 is made. A channel 4 reaches into the recess 2 from one end of the block, said channel 4 being narrower at the recess than at the end of the block, and said channel being provided with a shoulder 5 at the spot where the width is changed.

In the block, two small cavities 6, 7 and 8, 9 resp. are made on each side of the channel 4. Of these the two outer cavities 6, 9 are half the size of the inner ones 7, 8. The larger cavities 7 and 8 and the smaller cavities 6 and 9 are connected to the circular recess 2 through channels or restrictions 10. Furthermore, there is one small cavity 11 in the bottom 3 of the recess 2 in one of the two mould halves which are included in each sampling device.

When the two mould halves 1 are placed with the recesses 2 opposite each other said recesses will form a hollow provided with an entrance channel 4. A glass tube 12 made of heat resistant glass, e.g. quartz-glass, is located in the wider part of the channel 4 and against the shoulder 5. The mould mounted accordingly is then embedded in a known manner in a sand bed, which keeps the mould halves together, and after that the finished apparatus is provided with suitable equipment for its lowering down into the melt.

The entrance channel 12 may be provided with radial dents 13, of which three are shown in the drawing. If the sampling device is to be used for sampling from unkilled material, an adjusted amount of aluminum or other metal may be located in the tube 12, such as in the shape of a wire or a ring 14. The result will be that the dents 13 cause a proper mixing of the inpouring molten metal and the aluminum, which results in a properly killed sample.

In certain sampling operations in which samples are drawn directly from a casting jet, it may be necessary to locate the mould in a specific way and this location has to be identified on the resulting sample. For this reason one of the mould halves contains a small recess 11 which produces a projection on the sample, and a corresponding mark has to be provided, easily visible, on the actual sampling device, so that said sampling device can be located in the desired way.

The samples must practically always be marked with some code e.g. by stamping certain combinations of letters or figures, to be identified. Such an operation takes quite a lot of time. This marking may be facilitated if the code, prior to the sampling, is stamped onto a plate which is then easily fastened to the sample.

One way of fastening a metal plate to the sample consists of that the sample is provided with several small projections produced similarly to the mark for the above mentioned orientation. The plate is then put above the sample, against the small projections and a welding current is conducted through the sample and the plate. The plate will thus through spot or resistance welding be fastened to the sample in a quick and simple manner, which will save a great deal of time and make the sample reach the laboratory for analysis quicker than before.

The cavities 6 and 9 are of a size that they form hollows which contain 0.5 gram of the sample, and the cavities 7 and 8 contain 1 gram of the sample as they are double the size of the cavities 6 and 9.

At the sampling the sampling device is connected to a long handle, e.g. a roll made of several layers of paper, so that it can be lowered down into the melt. The sampling device is brought down into the melt with the entrance tube 12 first said entrance passage being protected against mechanical influence by a sleeve or cup-like member, and the outer end of said entrance tube preferably being covered by a housing which melts or dissolves due to the heat from the melt and thus opens the entrance to the mould. When the molten metal flows into the entrance tube 12 due to the ferrostatic pressure, the air is squeezed out through the parting line between the mould halves and out through the sand bed. In spite of the fact that there apparently should be difficulties in squeezing the air through the parting line and the sand bed, it has in reality turned out to work very well and the mould will quickly be filled with molten material. Another experience is that very little material leaks out into the parting line and that there is no presence of annoying casting burr. The small cavities 6, 7, 8, 9 may, however, be provided with very narrow vents.

After filling the mould, which takes about 5 seconds, it is opened and the glass tube is broken whereupon the cast sample is accesible. When marked, the samples are transported to the laboratory for analysis. The small pieces of 0.5 and 1 gram may be broken off for combustion methodical analysis of carbon sulphus etc. The formed disc which on the whole is without casting burr is braced in a machine for tooling of one side, which by certain samples is represented by the side provided with the boss.

The peg formed by the entrance tube 12 may be used as need arises. However it must be understood that if e.g. aluminum has been added for the killing of the sample, there is a little risk that the part of the sample which has been formed in the entrance tube 12 has not been completely killed, but that the aluminum has flown with the molten metal and mixed with said molten metal on the way, while the peg and especially the outer part of it consists of open material.

Since the disc substantially lacks casting burr and thus, may be braced without any foregoing tooling, for preparation of the side which will be analysed through spectrometry, and as easily detachable quantities of the sample having a given weight within the set up tolerance limits will be obtained directly, it will be a simple and quick step to perform the analysis of the obtained sample. It has also appeared that the small cavities which are created by the recesses 6, 7, 8, 9 provide very representative samples of the melt and contain properly killed material if e.g. aluminum has been added to the entrance tube 12 and said entrance tube is formed with dents 13 as illustrated in the drawing.

In the illustrated embodiment of the invention the mould consists of two halves which are on the whole identical and which are produced as blocks, said blocks being manufactured through machining or die-casting or powder metal forming. It is, however, possible to manufacture the mould halves from pressed metal sheets and it would also be possible to have the mould designed as one mould piece with a substantially flat cover. Nor is the shape of the recess 2 critical although the circular form is preferred. Furthermore the sampling mould according to the invention may be of a disposable or a permanent type.

We claim:
1. A sampling mould for drawing samples of molten material from pools of molten materials, said mould comprising two blocks located and fastened to each other, at least one of which is provided with a recess which forms a specimen, an entrance passage which permits said molten material to flow into said recess, said passage extending from one end of at least one of said blocks and into said recess, said passage being narrower in width at said recess than at said one end and being provided with a shoulder where said width is changed, a glass tube which extends into said entrance passage and rests upon said shoulder, said tube comprising a plurality of radial dents, and a plurality of disc-shaped cavities, positioned on each side of said passage, each of which forms a hollow in which a disc-shaped sample of a fixed size is formed, each of said disc-shaped cavities being connected to said recess through a narrow channel in which an elongated handle is formed connecting said respective sample with said specimen and by means of which said respective sample may be easily detached from said specimen.

2. Sampling mould as claimed in claim 1, characterized in that it consists of two substantially identical parts (1).

3. Sampling mould as claimed in claim 1, characterized in that the bottom (3) of the recess (2) is provided with a mark (11) in one of the two parts which form the mould.

4. Sampling mould as claimed in claim 1, characterized in that the outer end of the entrance tube (12) is covered with a housing, which melts or dissolves due to the heat from the melt and thus opens the inlet to the mould.

5. Sampling mould as claimed in claim 1, characterized in that the bottom (3) of the recess (2) is provided with small cavities, which supply the sample with corresponding projections for welding a marking plate thereto.

6. A sampling mould as claimed in claim 1 wherein said plurality of disc-shaped cavities includes at least one cavity forming a hollow which will hold 0.5 grams of said molten material and at least one other cavity forming a hollow which will hold 1 gram of said molten material.

* * * * *